US006475467B1

(12) United States Patent
Keller et al.

(10) Patent No.: US 6,475,467 B1
(45) Date of Patent: Nov. 5, 2002

(54) MEDICINAL AEROSOL FORMULATIONS

(75) Inventors: Manfred Keller, Bad Krozingen (DE); Kurt Herzog, Basel (CH); Rudi Müller-Walz, Schopfheim (DE); Holger Kraus, Rickenbach (CH)

(73) Assignee: Jago Research AG, Muttenz (CH)

( * ) Notice: Subject to any disclaimer, the term of this patent is extended or adjusted under 35 U.S.C. 154(b) by 0 days.

(21) Appl. No.: 09/744,798

(22) PCT Filed: Aug. 2, 1999

(86) PCT No.: PCT/CH99/00360

§ 371 (c)(1), (2), (4) Date: Apr. 20, 2001

(87) PCT Pub. No.: WO00/07567

PCT Pub. Date: Feb. 17, 2000

(30) Foreign Application Priority Data

Aug. 4, 1998 (CH) .............................................. 1633/98

(51) Int. Cl.[7] ............................ A61K 9/12; A61K 9/14; A61M 11/00

(52) U.S. Cl. ........................... 424/45; 424/46; 424/489; 128/200.14; 128/200.24

(58) Field of Search .......................... 424/283, 45, 451, 424/47, 46, 489; 128/200.14, 200.24

(56) References Cited

U.S. PATENT DOCUMENTS

| | | | | |
|---|---|---|---|---|
| 2,868,691 A | | 1/1959 | Porush et al. | |
| 3,014,844 A | | 12/1961 | Thiel et al. | |
| 4,139,607 A | | 2/1979 | Simons et al. | |
| 4,174,295 A | | 11/1979 | Bargigia et al. | |
| 4,397,836 A | | 8/1983 | Madrange et al. | |
| 4,405,598 A | | 9/1983 | Brown | |
| 4,409,237 A | * | 10/1983 | Cairns et al. | 424/283 |
| 5,225,183 A | | 7/1993 | Purewal et al. | |
| 5,698,630 A | | 12/1997 | Andersson | |
| 5,846,521 A | | 12/1998 | Somani et al. | |
| 6,131,566 A | * | 10/2000 | Ashurst et al. | 128/200.14 |

FOREIGN PATENT DOCUMENTS

| | | |
|---|---|---|
| CA | 2075058 | 1/1991 |
| CA | 2062854 | 3/1992 |
| CA | 2086492 | 12/1992 |
| DE | 2736500 | 2/1978 |
| DE | 4003272 | 8/1991 |
| EP | 0372777 | 6/1990 |
| EP | 0504112 | 3/1992 |
| EP | 0550031 | 12/1992 |
| EP | 0885943 | 12/1998 |
| FR | 2339604 | 6/1977 |
| IE | 91350 | 8/1991 |
| JP | 61158919 | 7/1986 |
| WO | 9104011 | 4/1991 |
| WO | 9111495 | 8/1991 |
| WO | 9200061 | 1/1992 |
| WO | 9317665 | 9/1993 |
| WO | 9401511 | 1/1994 |
| WO | 9403056 | 2/1994 |
| WO | 9619198 | 6/1996 |

OTHER PUBLICATIONS

RD–17066, Aerosol propellants comprising N2O and/or CO2 (Jun. 1978) (XP 002090730).

Derwent Abstract No. AN–86–228980, Drug composition for dermatophytosis (1986) (XP 002039614).

Derwent Abstract No. AN–89–184245, Aerosol pressure packs for administration of medicaments (1989) (XP 002039615).

* cited by examiner

*Primary Examiner*—Jose' G. Dees
*Assistant Examiner*—Mina Haghighation
(74) *Attorney, Agent, or Firm*—Selitto, Behr & Kim

(57) ABSTRACT

The use of solid, pharmaceutically acceptable salts of cromoglycic acid and/or nedocromil as carriers in a therapeutically and prophylactically inefficacious amount in suspension aerosol formulations of pharmaceutical active compounds improves the dispersion properties, increases the chemical and physical stability of moisture-sensitive active compounds, makes possible a more accurate dosage, in particular even of low-dose active compounds, and as a rule permits the abandonment of surface-active agents.

25 Claims, No Drawings

MEDICINAL AEROSOL FORMULATIONS

FIELD OF THE INVENTION

The present invention relates to medicinal suspension aerosol formulations and to a novel use of cromoglycic acid and nedocromil salts.

BACKGROUND OF THE INVENTION

For the preparation of medicinal metered-dose aerosols, as a rule suitable propellants are only those which can be liquefied at room temperature and which lead on successive spraying of the contents to no or only in any case to a slight decrease in the internal pressure in the container. In the past, customarily chlorofluorocarbons (CFCs), such as trichlorotrifluoromethane (F11), dichlorodifluoromethane (F12) and 1,2-dichloro-1,1,2,2-tetrafluoroethane (F114), and occasionally also short-chain alkanes, such as propane, butane and isobutane, were used.

On account of the ozone problem, caused by the elimination of free-radical chlorine atoms from CFCs, in the Montreal Agreement many countries have come to an understanding that they will no longer use CFCs as propellants in future. Gases, such as carbon dioxide, nitrogen and the like, can admittedly be liquefied under pressure, but are not utilizable as propellants for metered-dose aerosols, because the internal pressure in the container very greatly decreases with increasing emptying. However, fluorinated alkanes, in particular hydrofluoroalkanes (in the context of the present invention also designated "HFA") such as 1,1,1,2-tetrafluoroethane (HFA 134a) and 1,1,1,2,3,3,3-heptafluoropropane (HFA 227), have proved suitable CFC substitutes for the medicinal area, as they are inert and have a very low toxicity. On account of their physical properties, such as pressure, density etc., they are particularly suitable for replacing CFCs such as F11, F12 and F114 as propellants in metered-dose aerosols.

However, it has been shown that the customary excipients used in CFC-containing metered-dose aerosols, such as lecithin, sorbitan trioleate and oleic acid, are only inadequately soluble in hydrofluoroalkanes, such as HFA 134 and HFA 227. It has therefore been proposed either to improve the solubility in a manner known per se by use of a cosolvent such as ethanol or to coat the active compound particles with the surface-active agent or—instead of this—to dispense with a surface-active agent or to use special, propellant-soluble surface-active agents. These proposals are found, for example, in U.S. Pat. Nos. 2,868,691, 3,014 844, DE-A-2 736 500, EP-A-0 372 777, WO-A-91/11495, EP-A-0 504 112, EP-B-0 550 031, WO-A-91/04011, EP-A-0 504 112 and WO-A-92/00 061.

It is generally known that in the case of suspension formulations only active compound particles which are smaller than 6 μm are respirable. For the desired deposition of the active compounds in the lungs, these must therefore be comminuted or micronized by means of specific processes, such as pinned-disk, ball or air-jet mills. A grinding process, however, as a rule leads to an increase in surface area, which is accompanied by an increase in the electrostatic charge of the micronized active compound, whereby the flow behaviour and the active compound dispersion is then usually impaired. As a result of the interfacial and charge activities, there is frequently an agglomeration of active compound particles or alternatively adsorption of active compound at interfaces, which becomes conspicuous, for example, in the accumulation on equipment or container surfaces.

In aerosol preparations in which the active compound is present suspended in liquefied propellant, deposition or ring formation can occur in the container at the position where the liquid phase changes into the gas phase. Without wetting the micronized active compound particles or conducting away charges and modifying their surface properties, suspensions can only be inadequately stabilized or kept in a dispersed state. The lack of wetting or dispersion of the active compound particles also has the result that these in many cases have a high tendency for adsorption and stick to surfaces, such as the container inner wall or the valve, which then leads to an underdosage and to a poor dosage accuracy from puff of spray to puff of spray. In the case of suspensions, it is therefore as a rule necessary to add a surface-active excipient or a lubricant in order to lower the adsorption on interfaces and to achieve an acceptable dosage accuracy. A change or reduction in the proportion of the inhalable, respirable particles, the so-called fine particle dose (FPD), occurring in the course of storage, which leads to a decrease in the activity of the aerosol formulation, is particularly problematical.

To overcome these problems, as a rule permitted surface-active substances are added, as have already been used earlier in the CFC-containing formulations. Alternatively to this, in certain cases a modification of the surface properties by means of various measures (e.g. coating) can help to minimize these undesired effects. Because, however, surface-active agents such as oleic acid, sorbitan trioleate and lecithin only dissolve inadequately in hydrofluoroalkanes such as HFA 134a and/or HFA 227, a polar cosolvent such as ethanol is or must be added so that the pharmaceutical technology problems can be controlled better.

If, however, ethanol is added in a higher concentration, the density of the propellant mixture decreases, which can lead to an undesired demixing, especially in the case of suspensions. Moreover, a "wet spray" can undesirably be obtained, because the propellant evaporates much more rapidly than ethanol. In addition, however, as a result of the increase in the solubility during storage, dissolving effects can occur which then lead to crystal growth and in turn to a reduction in the amount of inhalable, respirable particles, the so-called fine particle dose (FPD).

It is additionally disadvantageous that in the case of ethanol concentrations of, for example, 10% or more, the proportion of inhalable particles (<6 μm) decreases, because the spray can produce particles having a greater aerodynamic diameter on account of the different evaporation properties of ethanol and the propellant. As a result of this, there is a reduction in the fine particle dose (FPD) crucial for the activity. This may explain why most commercially available metered-dose aerosols have been formulated as suspensions.

In the case of ethanol-containing aerosols, there are moreover also occasionally problems of active compound stability in the case of suspension formulations. In addition, the active compound stability, the active compound dispersion and the fine particle dose can also be adversely affected by moisture.

To measure the aerodynamic particle size distribution or the FPD or fine particle fraction (FPF), impactors, such as the 5-stage multistage liquid impinger (MSLI) or 8-stage Andersen cascade impactor (ACI), which are described in Chapter <601> of the United States Pharmacopeia (USP) or in the inhalants monograph of the European Pharmacopeia (Ph. Eur.) are suitable. By means of the aerodynamic particle distribution, it is possible by means of a so-called "logprobability plot" (logarithmic representation of the probability distribution) to calculate the mean aerodynamic particle diameter (median mass aerodynamic diameter (MMAD)) of aerosol preparations. Using this information on particle distribution, information is obtained as to whether the active compound is more easily deposited in the upper or lower area of the lungs.

As follows from the preceding text, adherence to a high dosage accuracy, i.e. the constant release of active compound from puff of spray to puff of spray, is a fundamental problem of suspension metered-dose aerosols, which is made additionally difficult by the replacement of CFCs. In addition to the valve and actuator, the dosage accuracy essentially depends on the suspension properties, i.e. on how easily and homogeneously the active compound is dispersed in the propellant and how long the suspension remains in this labile equilibrium state without change in its physical properties. The maintenance of a high dosage accuracy in the case of potent, low-dose active compounds proves particularly difficult. For example, for the long-acting beta-agonist formoterol fumarate, which is already therapeutically active in very low doses (6 μg/stroke), a formulation is needed which affords an adequately stable suspension which does not adhere to interfaces and does not change in the course of storage under different temperature and moisture conditions. A general survey of the products found on the market shows that to date there is no metered-dose aerosol which can meter active compounds in amounts of less than 10 μg per stroke (i.e. per puff of spray) with a mean variation of better than ±25%.

SUMMARY OF THE INVENTION

The invention is therefore based on the object of avoiding the mentioned problems of suspension metered-dose aerosols to the greatest possible extent, and in particular of making available a medicinal suspension aerosol formulation which has improved suspension and shelf-life properties, suppresses to the greatest possible extent the disadvantageous effect of water on the stability and dispersion of active compounds and permits a high dosage accuracy—even in the case of low-dose active compounds.

The object is achieved according to the invention by a medicinal aerosol formulation, comprising a solid, pharmaceutically acceptable salt of cromoglycic acid and/or nedocromil in a therapeutically and prophylactically inefficacious amount, an efficacious amount of a finely divided pharmaceutically active compound which is different therefrom, having a mean particle diameter of less than 6 μm, and a non-toxic liquid propellant, in which the active compound is present in suspended form.

DETAILED DESCRIPTION OF THE INVENTION

It has in fact surprisingly been found that the addition of cromoglycic acid and/or nedocromil salts in subtherapeutic concentrations of, for example, 5–100 μg/stroke is very helpful in suspending pharmaceutically active compounds in hydrofluoroalkanes and other propellants. These substances, so-called mast cell inhibitors, have been employed until now in the form of their sodium salts in topical preparations (eye drops, nasal sprays) and as antiallergics in inhalation products. For example, FR-A-2 339 604 discloses disodium cromoglycate having a water content of less than 5% by weight and aerosol formulations having a water content of less than 1% by weight which contain 1–20% by weight of finely divided disodium cromoglycate and, as a propellant, preferably CFCs such as F11, F12 and F114. In WO-A-91/11495, propellant mixtures which contain a partly fluorinated lower alkane such as HFA 227, HFA 125, HFA 134a or HFA 152a, and powder aerosols based on such propellant mixtures are described, suitable pharmaceuticals, inter alia antiallergics such as disodium cromoglycate and nedocromil and furthermore also active compound combinations of disodium cromoglycate with betamimetics or PAF antagonists being mentioned as examples. In WO-A-92/00061, aerosol formulations comprising a fluorocarbon propellant, a polyethoxylated surface-active agent and a medicament are disclosed, where the medicament used can preferably be the salt of a dicarboxylic acid, for example a salt of nedocromil or cromoglycic acid. In the previously known formulations, the cromoglycic acid or nedocromil salts, however, are in each case employed in inhalable form and in a therapeutically and/or prophylactically active concentration.

In commercial applications, disodium cromoglycate is employed in metered-dose aerosols in concentrations of 1 mg and 5 mg/stroke and in inhalation solutions and powders in concentrations of 20 mg per application. Such products are obtainable under the trade name Intal® (Fisons) and are also supplied as generics by various firms. Nedocromil sodium is therapeutically employed as Tilade® metered-dose aerosol (Fisons) in a concentration of 2 mg/stroke. In addition, there are also combination products of the anti-allergic disodium cromoglycate and a beta-agonist, which contain 1 mg of disodium cromoglycate and, for example, 0.5 mg of reproterol hydrochloride (Aarane® from Fisons, Allergospasmin® from Asta Medica) or 0.05 mg of fenoterol hydrobromide (Ditec® from Thomae) per puff of spray.

Surprisingly, it has further been found that instead of known carriers permitted for inhalation, such as lactose or glucose, the high-dose active compounds cromoglycic acid and nedocromil can be used as carriers if these are employed in subtherapeutic doses in the form of their salts. Pharmaceutically acceptable salts of both substances are suitable for protecting other active compounds and for obtaining metered-dose aerosols having advantageous product properties. If a pharmaceutically active compound such as formoterol fumarate is mixed with a pharmaceutically acceptable salt of cromoglycic acid and/or nedocromil as a carrier, a powder mixture is obtained which can usually also be readily suspended in the customary propellants without a surface-active agent. The anionic carrier materials according to the invention, which can be present, for example, in the form of their sodium salts, form associations, on account of their chemical charges, with active compounds, such as formoterol fumarate, levalbuterol sulfate and the like, which can also be accurately metered in very low dosages.

Surprisingly, it has additionally been found that salts of cromoglycic acid and nedocromil, such as disodium cromoglycate and nedocromil sodium, improve the chemical and physical stability of moisture-sensitive active compounds, such as levalbuterol sulfate, formoterol fumarate and the like, which possibly could be attributed to their hygroscopicity, in that they keep away the negative influence of the water on moisture-sensitive active compounds to a certain extent.

The tendency to adhesion, of electrostatically charged active compounds such as micronized corticosteroids is moreover reduced by admixture of salts of cromoglycic acid and/or nedocromil, such as disodium cromoglycate and/or nedocromil sodium, and their dispersion properties are improved.

The use according to the invention of pharmaceutically acceptable salts of cromoglycic acid and/or nedocromil as carrier materials in therapeutically and prophylactically inefficacious amounts therefore permits the preparation of improved suspension aerosol formulations, it being possible, if desired, to dispense completely or largely with excipients such as oleic acid, sorbitan trioleate, lecithin, lactose and glucose, which dissolve only inadequately or not at all in hydrofluoroalkanes such as HFA 134a and HFA 227. A further advantage of the carrier materials used according to the inventions is that the sodium salts are already permitted as active compounds in a relatively high dose and thus expensive safety tests for the demonstration of their harmlessness are unnecessary.

The aerosol formulation according to the invention is fundamentally suitable for any desired pharmaceutically active compounds which can be administered as suspension aerosols in therapeutically or prophylactically efficacious amounts in each case. Examples of preferred active compounds are beta-mimetics, anticholinergics, antiallergics and anti-inflammatory active compounds (e.g. corticosteroids, leukotriene antagonists, cytokinin inhibitors, calcium channel openers etc.). Formulations are particularly preferred which as pharmaceutically active compound contain formoterol, salmeterol, fenoterol, clenbuterol, levalbuterol, ipratropium, oxitropium, glycopyrronium, tiotropium, budesonide, ciclesonide, mometasone, fluticasone, beclomethasone, flunisolide, loteprednol, triamcinolone, amiloride, rofleponide or a pharmaceutically acceptable salt or derivative of these active compounds, such as formoterol fumarate, formoterol tartrate, salmeterol xinafoate, fenoterol hydrobromide, clenbuterol hydrochloride, ipratropium bromide, oxitropium bromide, glycopyrronium bromide, tiotropium bromide, mometasone furoate, fluticasone dipropionate, beclomethasone dipropionate or flunisolide acetate, where optically active active compounds can be used in the form of their active isomer or as an isomer mixture (e.g. racemate). If desired, the aerosol formulations according to the invention can also contain two or more pharmaceutically active compounds, combinations of fluticasone, ipratropium, oxitropium, glycopyrronium, tiotropium, budesonide, mometasone, ciclesonide, rofleponide or a pharmaceutically acceptable salt or derivative thereof with levalbuterol, formoterol and/or salmeterol or a pharmaceutically acceptable derivative thereof being preferred. If desired, the aerosol formulations according to the invention can also contain dissolved active compounds; it is only essential to the invention that at least one pharmaceutically active compound is present in suspended form. As follows from the explanations below, however, pharmaceutically acceptable cromoglycic acid and nedocromil salts according to the invention are only used as carriers, i.e. the "pharmaceutically active compound" in the context of the present invention is not a pharmaceutically acceptable salt of cromoglycic acid or nedocromil.

The aerosol formulation according to the invention is particularly advantageous for the administration of low-dose active compounds. The invention therefore in particular also relates to aerosol formulations of active compounds which can be administered in an efficacious dose of approximately 0.1 to 100 μg per puff of spray, those with a dose of at most approximately 50 μg being preferred and those with a dose of approximately 0.1 to 20 μg being particularly preferred. The stroke masses of commercially available MDIs (metered-dose inhalers) are usually in the range from approximately 30 to 130 mg (with valves correspondingly from approximately 25 to 100 μl) and are typically approximately 70 mg per puff of spray. Accordingly, the preferred aerosol formulations of low-dose active compounds as a rule contain approximately 0.0001 to 0.2% by weight, in particular at most approximately 0.1% by weight and particularly preferably approximately 0.0001 to 0.04% by weight, of suspended active compound.

The active compound to be suspended or the active compounds to be suspended can be micronized in a manner known per se, e.g. by means of pinned-disk, ball or air-jet mills or obtained by controlled microcrystallization or precipitation and suspended in the propellant. Expediently, the mean particle diameter of the active compound particles should be at least 6 μm and preferably at least approximately 1 μm, the "mean particle diameter" in the context of the present invention designating the mean (mass mean) aerodynamic particle diameter known as the median mass aerodynamic diameter (MMAD).

The salts of cromoglycic acid or nedocromil used as carriers can preferably likewise be present in the aerosol formulations according to the invention in suspended form having an mean particle diameter of less than 6 μm (preferably at least approximately 1 μm) They can be micronized to the desired particle size in a manner known per se, either on their own or together with the pharmaceutically active compound or the pharmaceutically active compounds, and suspended in the propellant. If desired, the cromoglycic acid and nedocromil salts, however, can also be used in a relatively large particle size if it is desired that these salts are not sprayed or do not pass into the lungs.

Suitable carriers are in principle all pharmaceutically acceptable salts of cromoglycic acid or of nedocromil in which one or both carboxyl groups are present in deprotonated, i.e. anionic, form. The alkali metal salts and the alkaline earth metal salts can preferably be used, in particular the sodium and potassium salts, disodium cromoglycate and nedocromil sodium being particularly preferred.

Disodium cromoglycate and nedocromil sodium are used—as mentioned above—in known metered-dose aerosols in a therapeutically or prophylatically efficacious amount of customarily 1 mg or 2 mg per puff of spray. In contrast, the pharmaceutically acceptable salts of cromoglycic acid and of nedocromil are not used according to the invention as therapeutic or prophylactic active compounds, but merely as carriers and accordingly only in amounts which have no significant therapeutic or prophylactic action. The amounts of cromoglycic acid salts or nedocromil salts used according to the invention are therefore as a rule not over 500 μg per puff of spray, where in general amounts of approximately 5 to 250 μg, in particular approximately 10 to 100 μg, per puff of spray are preferred. The proportion of cromoglycic acid salts or nedocromil salts in the aerosol formulations according to the invention is therefore as a rule not over approximately 0.7% by weight and is preferably approximately 0.007 to 0.36% by weight, in particular approximately 0.015 to 0.15% by weight, based on the total formulation.

Based on the suspended active compound, the proportion of cromoglycic acid and nedocromil salts can vary within a relatively wide range. In general, however, the weight ratio of the cromoglycic acid salts and/or nedocromil salts to the suspended pharmaceutically active compound or to the suspended pharmaceutically active compounds is approximately 10:1 to approximately 1:10, preferably approximately 5:1 to approximately 1:5.

Preferably, the cromoglycic acid and/or nedocromil salt can be selected in comparison to the pharmaceutically active compound such that the density of these materials is comparable overall with the density of the propellant. For example, micronized formoterol fumarate, which tends to float in HFA 227, can be combined with disodium cromoglycate, which tends to sediment, in order to keep the suspended material better in suspension and to minimize flotation or sedimentation.

Suitable non-toxic liquid propellants for the aerosol formulations according to the invention are in principle all pressure-liquefied propellants which can be used customarily in metered-dose aerosols, for example fluorochlorocarbons such as trichloro-monofluoromethane (F11), dichlorodifluoromethane (F12), monochlorotrifluoromethane (F13), dichloro-monofluoromethane (F21), monochlorodifluoromethane (F22), monochloromonofluoromethane (F31), 1,1,2-trichloro-1,2,2-trifluoroethane (F113), 1,2-dichloro-1,1,2,2-tetrafluoroethane (F114), 1-chloro-1,1,2,2,2-pentafluoroethane (F115), 2,2-dichloro-1,1,1-trifluoroethane (F123), 1,2-dichloro-1,1,2-trifluoroethane (F123a), 2-chloro-1,1,1,2-tetrafluoroethane (F124), 2-chloro-1,1,2,2-tetrafluoroethane (F124a), 1,2-dichloro-1,1-difluoroethane (F132b), 1-chloro-1,2,2-trifluoroethane (F133), 2-chloro-1,1,1-trifluoroethane (F133a), 1,1-dichloro-1-fluoroethane (F141b) and 1-chloro-1,1-difluoroethane (F142*b*), alkanes such as propane, butane and isobutane, fluorinated alkanes such as octafluoropropane (F218) and in particular hydrofluoroalkanes such as difluoromethane (HFA 32), pentafluoroethane (HFA 125), 1,1,2,2-tetrafluoroethane (HFA 134), 1,1,1,2-tetrafluoroethane (HFA 134a), 1,1,2-trifluoroethane (HFA 143), 1,1,1-trifluoroethane (HFA 143a), difluoroethane (HFA 152a), 1,1,1,2,3,3,3-heptafluoropropane (HFA 227) and the like.

Preferred propellants are the hydrofluoroalkanes of the general formula.

$$C_xH_yF_z \qquad (I)$$

in which x is the number 1, 2 or 3, y and z are each an integer ≧1 and y+z=2x+2.

As a rule, those hydrofluoroalkanes of the formula I in which x is the number 2 or 3 are particularly suitable.

Particularly preferred aerosol formulations are those which contain HFA 134 or HFA 227 or mixtures of these two propellants. HFA 134a and HFA 227 have a vapor pressure of about 6 bar and about 4.2 bar respectively at 20° C. Both propellants differ with respect to their density (about 1.2 g/ml for HFA 134a and about 1.4 g/ml for HFA 227), which is important insofar as it is possible by suitable choice of the propellant or propellant mixture to match its density better to the density of the suspended substances and thus to keep the latter better in suspension. If desired, the density of the propellant can be further reduced by addition of cosolvents or other propellants, such as ethanol, diethyl ether, propane, n-butane or isobutane.

The aerosol formulations according to the invention can preferably contain one or more hydrofluoroalkanes of the formula I, particularly preferably 1,1,1,2-tetrafluoroethane (HFA 134a) and/or 1,1,1,2,3,3,3-heptafluoropropane (HFA 227), and their proportion in the total formulation can preferably be at least approximately 50% by weight and particularly preferably at least approximately 80% by weight. As a rule, it is advantageous to employ these propellants in an amount of 90% by weight or more.

If desired, the aerosol formulations according to the invention can contain nitrogen or in particular dinitrogen monoxide (laughing gas) and/or carbon dioxide in an amount of approximately 0.0001 to 10% by weight as a further propellant. Concentrations of approximately 0.01 to 3% by weight are in general preferred and concentrations of approximately 0.1 to 1.0% by weight are particularly preferred; higher concentrations are as a rule only useful if the formulation contains a comparatively high proportion of cosolvents. It has in fact surprisingly been found that propellants with more advantageous properties can be obtained if a small amount of dinitrogen monoxide and/or carbon dioxide is added to the customary propellants, in particular to the hydrofluoroalkanes mentioned. Propellant mixtures of this type—in contrast to dinitrogen monoxide and carbon dioxide as the sole propellants—show only a slight decrease in the internal pressure in the container as it becomes more empty, which makes possible their use as propellants for metered-dose aerosols. Moreover, it has surprisingly been found that the addition of dinitrogen monoxide and/or carbon dioxide facilitates the suspension of pharmaceutical active compounds, whereby the addition of surface-active substances and/or cosolvents can be more easily dispensed with or at least the proportion thereof can be reduced. In addition, it has been found that by addition of dinitrogen monoxide and/or carbon dioxide, the undesired deposition of active compound in the oropharynx can be reduced and at the same time the fine particle dose can be increased. Furthermore, by addition of these propellants oxygen can be displaced from the hydrofluoroalkanes or other propellants, which improves the storage stability of oxidation-sensitive active compounds, and, depending on the amount of dinitrogen monoxide and/or carbon dioxide, the internal pressure in the aerosol container can be adjusted in such a way as is most useful for the particular application.

In general, aerosol formulations are preferred which have a pressure of approximately 3 to 10 bar, in particular approximately 3.5 to 6 bar, at 20° C. When using cosolvents or propellants having a low vapor pressure, a pressure which is in any case lower can preferably be correspondingly increased by addition of dinitrogen monoxide and/or carbon dioxide.

The aerosol formulations according to the invention can be prepared in a manner known per se by adding the propellant to the micronized pharmaceutically active compound and a pharmaceutically acceptable salt of cromoglycic acid and/or nedocromil and, if desired, introducing dinitrogen monoxide and/or carbon dioxide under pressure. These steps can in principle be carried out in any desired sequence. When using dinitrogen monoxide and/or carbon monoxide, however, as a rule it is preferred firstly to introduce this/these into the propellant and then to add the micronized active compound and the cromoglycic acid and/or nedocromil salt. The formulations can be prepared using customary stirrers and homogenizers. For dispensing, known processes, such as the cold- or pressure-filling technique or modifications of these techniques, can be employed. Suitable containers are, for example, pressure-resistant containers made of glass, plastic or aluminum, which can be equipped with metered-dose valves of, for example, 10 to 140 μl and can be provided with commercially available—also inspiration-triggered—mouth tube adapters.

Although the addition of cosolvents and surface-active agents is usually unnecessary as a result of the use of cromoglycic acid and/or nedocromil salts and in any case as a result of the use of dinitrogen monoxide and/or carbon dioxide, the addition of a small amount of cosolvent can occasionally be advantageous. Suitable cosolvents are, for example, water, alcohols having 1 to 3 carbon atoms, alkanes having 3 to 6 carbon atoms and dialkyl ethers having 2 to 4 carbon atoms. Examples of preferred cosolvents are:

ethanol, propanol, isopropanol, ethylene glycol, propylene glycol, glycerol, propane, butane, isobutane, pentane, dimethyl ether and diethyl ether, with ethanol, glycerol, propylene glycol and diethyl ether or mixtures thereof and in particular ethanol as a rule being particularly preferred. Preferred cosolvent mixtures using which a glidant action is simultaneously achieved are ethanol together with glycerol and/or propylene glycol and also diethyl ether together with glycerol and/or propylene glycol. In general, the proportion of cosolvents, if present, is not over approximately 15% by weight, preferably not over approximately 10% by weight and usually not over approximately 5% by weight, based on the total formulation.

The aerosol formulations according to the invention can preferably be essentially free of surface-active agents, i.e. preferably contain less than approximately 0.0001% by weight of surface-active agents. If desired, however, they can contain surface-active agents such as oleic acid, lecithin, sorbitan trioleate, cetylpyridinium chloride, benzalkonium chloride, polyoxyethylene (20) sorbitan monolaurate, polyoxyethylene (20) sorbitan monostearate, polyoxyethylene (20) sorbitan monooleate, polyoxypropylene/polyoxyethylene block copolymers, polyoxypropylene/polyoxyethylene/ethylenediamine block copolymers, ethoxylated castor oil and the like, where the proportion of surface-active agents, if present, can preferably be approximately 0.0001 to 1% by weight, in particular approximately 0.001 to 0.1% by weight, based on the total formulation.

Furthermore, if desired, the aerosol formulations according to the invention can contain buffer substances or stabilizers such as citric acid, ascorbic acid, sodium EDTA, vitamin E, N-acetylcysteine and the like. In general, such substances, if present, are used in amounts of not more than approximately 1% by weight, for example in an amount of from approximately 0.0001 to 1% by weight, based on the total formulation.

The use according to the invention of cromoglycic acid and/or nedocromil salts thus permits the preparation of improved suspension aerosol formulations of pharmaceutically active compounds, in particular of low-dose active compounds. The invention therefore likewise relates to the use of a solid, pharmaceutically acceptable salt of cromoglycic acid and/or nedocromil in a therapeutically and prophylactically inefficacious amount in a medicinal suspension aerosol formulation for reducing undesired adsorption or for improving the dosage accuracy and/or reducing the moisture sensitivity of a suspended pharmaceutical active compound.

Using the formulation technology according to the invention, it is thus possible to prepare active compounds or active compound combinations as metered-dose aerosols having more advantageous properties, as is further illustrated below by means of some examples.

EXAMPLE 1

6 g of micronized formoterol fumarate and 12 g of micronized disodium cromoglycate are weighed into a pressure addition vessel. After closing and evacuating the addition vessel, 35 g each of HFA 134a and HFA 227, which have previously been treated with 3% by weight of ethanol in another pressure addition vessel, are added with stirring. After homogenization, the suspension obtained is dispensed by means of the pressure-filling technique into aluminum containers sealed with metered-dose valves.

EXAMPLE 2

2 g of micronized ipratropium bromide and 10 g of micronized disodium cromoglycate are mixed and weighed into a pressure addition vessel. After closing and evacuating the addition vessel, 10 kg of HFA 227, which have previously been aerated with carbon dioxide in another pressure addition vessel and adjusted to a pressure of 5 bar at 20°C., are added. After homogenizing this mixture, the suspension obtained is dispensed by means of the pressure-filling technique into aluminum containers sealed with metered-dose valves.

EXAMPLE 3

2.5 g of micronized glycopyrronium bromide and 2.5 g of micronized nedocromil sodium are mixed and weighed into a pressure addition vessel. After closing and evacuating the addition vessel, 10.5 kg of a propellant mixture of HFA 227 and HFA 134a (weight ratio 90:10), which have previously been treated with 1% by weight of ethanol in another pressure addition vessel and aerated with dinitrogen oxide and adjusted to a pressure of 5.5 bar at 20° C., are added. After homogenizing this mixture, the suspension obtained is dispensed by means of the pressure-filling technique into aluminum containers sealed with metered-dose valves.

EXAMPLE 4

A powder mixture, consisting of 5 g of micronized formoterol fumarate, 20 g of micronized glycopyrronium bromide and 25 g of micronized disodium cromoglycate, is weighed into a pressure addition vessel. After closing and evacuating the addition vessel, 70 g of HFA 227, which have previously been treated with 2% by weight of ethanol in another pressure addition vessel and aerated with dinitrogen oxide and adjusted to a pressure of 5 bar at 20° C., are added with stirring. After homogenization, the suspension obtained is dispensed by means of the pressure-filling technique into aluminum containers sealed with metered-dose valves.

EXAMPLE 5

2.5 g of micronized glycopryrronium bromide, 5 g of micronized levalbuterol and 5 g of micronized nedocromil sodium are weighed into a pressure addition vessel. After closing and evacuating the addition vessel, 10.5 kg of a propellant mixture of HFA 227 and HFA 134a (weight ratio 80:20), which have previously been aerated in another pressure addition vessel with dinitrogen oxide and adjusted to a pressure of 5.25 bar at 20° C., are added. After homogenizing this mixture, the suspension obtained is dispensed by means of the pressure-filling technique into aluminum containers sealed with metered-dose valves.

EXAMPLE 6

5 g of micronized formoterol fumarate, 30 g of micronized fluticasone propionate and 10 g of micronized disodium cromoglycate are weighed into a pressure addition vessel. After closing and evacuating the addition vessel, 70 kg of HFA 227, which have previously been treated with 2% by weight of ethanol in another pressure addition vessel and aerated with dinitrogen oxide and adjusted to a pressure of 5 bar at 20° C., are added with stirring. After homogenization, the suspension obtained is dispensed by means of the pressure-filling technique into aluminum containers sealed with metered-dose valves.

EXAMPLE 7

20 g of micronized tiotropium bromide and 10 g of micronized nedocromil sodium are weighed into a pressure addition vessel. After closing and evacuating the addition vessel, 70 kg of a propellant mixture of HFA 227 and HFA 134a (weight ratio 70:30), which have previously been treated with 0.5% by weight of ethanol in another pressure addition vessel, are added with stirring. After homogenization, the suspension obtained is dispensed by means of the pressure-filling technique into aluminum containers sealed with metered-dose valves.

EXAMPLE 8

3 g of micronized glycopyrronium bromide, 3 g of micronized salmeterol xinafoate and 3 g of micronized disodium cromoglycate are mixed and weighed into a pressure addition vessel. After closing and evacuating the addition vessel, 10.5 kg of a propellant mixture of HFA 227 and HFA 134a (weight ratio 75:25), which have previously been aerated with dinitrogen oxide in another pressure addition vessel and adjusted to a pressure of 5.25 bar, are added. After homogenizing this mixture, the suspension obtained is dispensed by means of the pressure-filling technique into aluminum containers sealed with metered-dose valves.

EXAMPLE 9

A powder mixture, consisting of 10 g of micronized budesonide and 1 g of micronized disodium cromoglycate, is weighed into a pressure addition vessel. After closing and evacuating the addition vessel, 7 kg of a propellant mixture of HFA 227 and HFA 134a (weight ratio 65:35), which have previously been treated with 1% by weight of ethanol in another pressure addition vessel, are added with stirring. After homogenization, the suspension obtained is dispensed by means of the pressure-filling technique into aluminum containers sealed with metered-dose valves.

EXAMPLE 10

0.5 g of micronized formoterol fumarate and 2.0 g of micronized disodium cromoglycate are weighed into a pressure addition vessel. After closing and evacuating the addition vessel, 7.0 kg of HFA 227, which have previously been treated with 3% by weight of ethanol and 0.02% by weight of glycerol and aerated with dinitrogen oxide and adjusted to a pressure of 5 bar at 20° C. in another pressure addition vessel, are added with stirring. After homogenization, the suspension obtained is dispensed by means of the pressure-filling technique into aluminum containers sealed with metered-dose valves.

EXAMPLE 11

A powder mixture, consisting of 10 g of micronized budesonide, 0.5 g of micronized formoterol tartrate and 1 g of disodium cromoglycate, is weighed into a pressure addition vessel. After closing and evacuating the addition vessel, 70 kg of HFA 227, which have previously been treated in another pressure addition vessel with 2% by weight of ethanol and 0.2% by weight of propylene glycol, are added with stirring. After homogenization, the suspension obtained is dispensed by means of the pressure-filling technique into aluminum containers sealed with metered-dose valves.

EXAMPLE 12

A powder mixture, consisting of 0.5 g of micronized formoterol tartrate, 10 g of micronized fluticasone dipropionate and 1 g of micronized disodium cromoglycate, is weighed into a pressure addition vessel. After closing and evacuating the addition vessel, 7 kg of HFA 227, which have previously been treated with 2% by weight of diethyl ether and 0.02% by weight each of benzalkonium chloride, citric acid and propylene glycol in another pressure addition vessel, are added with stirring. After homogenization, the suspension obtained is dispensed by means of the pressure-filling technique into aluminum containers sealed with metered-dose valves.

EXAMPLE 13

3 g of micronized glycopyrronium bromide, 3 g of micronized salmeterol xinafoate, 3 g of micronized disodium cromoglycate, 0.03 g of sodium EDTA and 0.03 g of glycerol are mixed and weighed into a pressure addition vessel. After sealing and evacuating the addition vessel, 10.5 kg of a propellant mixture of HFA 227 and HFA 134a (weight ratio 75:25), which have previously been aerated with dinitrogen oxide and adjusted to a pressure of 5.25 bar in another pressure addition vessel, are added. After homogenizing this mixture, the suspension obtained is dispensed by means of the pressure-filling technique into aluminum containers sealed with metered-dose valves.

What is claimed is:

1. A medicinal aerosol formulation, comprising a solid, pharmaceutically acceptable salt of at least one compound selected from the group consisting of cromoglycic acid and nedocromil, in a therapeutically and prophylactically inefficacious amount in the range from 5 to 250 μg per puff of spray, an efficacious amount of a finely divided pharmaceutically active compound which is different from said salt, having a mean particle diameter of less than 6 μm, and a non-toxic liquid propellant, in which said active compound is present in suspended form.

2. The aerosol formulation as claimed in claim 1, wherein said salt is selected from the group consisting of alkali metal salts and alkaline earth metal salts.

3. The aerosol formulation as claimed in claim 1, wherein said salt is selected from the group consisting of disodium cromoglycate and nedocromil sodium.

4. The aerosol formulation as claimed in claim 1, wherein said salt is present in suspended form having a particle size of less than 6 μm.

5. The aerosol formulation as claimed in claim 1, wherein said salt is present in an amount of from 10 to 100 μg, per puff of spray.

6. The aerosol formulation as claimed in claim 1, wherein said salt and said suspended pharmaceutically active compound are present in a weight ratio of said salt to the suspended pharmaceutically active compound of from 10:1 to 1:10.

7. The aerosol formulation as claimed in claim 1, wherein said pharmaceutically active compound is selected from the group consisting of beta-mimetics, anticholinergics, antiallergics and antiinflammatory active compounds.

8. The aerosol formulation as claimed in claim 1, wherein said pharmaceutically active compound is selected from the group consisting of formoterol, salmeterol, fenoterol, clenbuterol, levalbuterol, ipratropium, oxitropium, glycopyrronium, tiotropium, budesonide, ciclesonide, mometasone, fluticasone, beclomethasone, flunisolide, loteprednol, triamcinolone, amiloride, rofleponide and pharmaceutically acceptable salts and derivatives thereof.

9. The aerosol formulation as claimed in claim 1, wherein the suspended active compound is present in an amount of from 0.0001% to 0.2% by weight, based on the total weight of the formulation.

10. The aerosol formulation as claimed in claim 1, wherein said pharmaceutically active compound comprises at least one compound selected from the group consisting of fluticasone, ipratropium, oxitropium, glycopyrronium, tiotropium, budesonide, mometasone, ciclesonide, rofleponide and pharmaceutically acceptable salts and derivatives thereof, and the aerosol formulation further comprising an active compound selected from the group consisting of levalbuterol, formoterol, salmeterol and pharmaceutically acceptable derivatives thereof.

11. The aerosol formulation as claimed in claim 1, wherein the propellant comprises one or more hydrofluoroalkanes of formula $$C_xH_yF_z \quad (I)$$

in which x is 1, 2 or 3, y and z are each an integer ≧1 and y+z=2x+2.

12. The aerosol formulation as claimed in claim 1, wherein said propellant comprises at least one compound selected from the group consisting of 1,1,1,2-tetrafluoroethane and 1,1,1,2,3,3,3-heptafluoropropane.

13. The aerosol formulation as claimed in claim 1, further comprising at least one compound selected from the group consisting of dinitrogen monoxide and carbon dioxide in an amount of from 0.0001% to 10% by weight, based on the total weight of the formulation.

14. The aerosol formulation as claimed in claim 1, having a pressure of 3 to 10 bar at 20° C.

15. The aerosol formulation as claimed in claim 1, further comprising a cosolvent.

16. The aerosol formulation as claimed in claim 15, comprising at most 15% by weight of said cosolvent, based on the total weight of the formulation.

17. The aerosol formulation as claimed in claim 1, being essentially free of surface-active agents.

18. The aerosol formulation as claimed in claim 1, wherein said salt is selected from the group consisting of sodium salts and potassium salts.

19. The aerosol formulation as claimed in claim 1, wherein said salt and said suspended pharmaceutically active compound are present in a weight ratio of said salt to said suspended pharmaceutically active compound of from 5:1 to 1:5.

20. The aerosol formulation as claimed in claim 1, wherein said suspended pharmaceutically active compound is present in an amount of from 0.0001% to 0.1% by weight, based on the total weight of the formulation.

21. The aerosol formulation as claimed in claim 1, further comprising at least one compound selected from the group consisting of dinitrogen monoxide and carbon dioxide in an amount of from 0.01% to 3% by weight, based on the total weight of the formulation.

22. The aerosol formulation as claimed in claim 1, having a pressure of 3.5 to 6 bar at 20° C.

23. The aerosol formulation as claimed in claim 15, wherein said cosolvent is at least one compound selected from the group consisting of ethanol, glycerol, propylene glycol and diethyl ether.

24. A method of improving dosage accuracy of a medicinal suspension aerosol formulation comprising a finely divided pharmaceutically active compound having a mean particle diameter of less than 6 μm, and a non-toxic liquid propellant, in which the active compound is present in suspended form, said method comprising adding to said formulation a solid, pharmaceutically acceptable salt of at least one compound selected from the group consisting of cromoglycic acid and nedocromil, in a therapeutically and prophylactically inefficacious amount.

25. A method of reducing moisture sensitivity of a suspended pharmaceutically active compound in a medicinal suspension aerosol formulation comprising said pharmaceutically active compound in finely divided form having a mean particle diameter of less than 6 μm, and a non-toxic liquid propellant, in which said active compound is present in suspended form, said method comprising adding to said formulation a solid, pharmaceutically acceptable salt of at least one compound selected from the group consisting of cromoglycic acid and nedocromil, in a therapeutically and prophylactically inefficacious amount.

* * * * *